United States Patent
Weel-Sneve et al.

(10) Patent No.: US 9,217,152 B2
(45) Date of Patent: Dec. 22, 2015

(54) DINQ-SRNA TYPE I TOXIN-ANTITOXIN SYSTEM FOR PLASMID MAINTENANCE

(75) Inventors: Ragnhild Weel-Sneve, Oslo (NO); James Booth, Oslo (NO); Magnar Bjoras, Oslo (NO); Knut Ivan Kristiansen, Oslo (NO)

(73) Assignee: Oslo Universitetssykehus HF, Oslo (NO)

( * ) Notice: Subject to any disclaimer, the term of this patent is extended or adjusted under 35 U.S.C. 154(b) by 0 days.

(21) Appl. No.: 13/988,740

(22) PCT Filed: Nov. 23, 2011

(86) PCT No.: PCT/EP2011/070852
§ 371 (c)(1),
(2), (4) Date: Sep. 10, 2013

(87) PCT Pub. No.: WO2012/069551
PCT Pub. Date: May 31, 2012

(65) Prior Publication Data
US 2014/0004602 A1   Jan. 2, 2014

(30) Foreign Application Priority Data
Nov. 23, 2010 (EP) .................................. 10192306

(51) Int. Cl.
*C12N 15/68* (2006.01)
*C12N 15/65* (2006.01)
*C07K 14/31* (2006.01)

(52) U.S. Cl.
CPC ................ *C12N 15/65* (2013.01); *C07K 14/31* (2013.01); *C12N 15/68* (2013.01)

(58) Field of Classification Search
None
See application file for complete search history.

(56) References Cited

U.S. PATENT DOCUMENTS

| 6,703,233 B1 | 3/2004 | Galen |
| 7,125,720 B2 | 10/2006 | Galen |
| 7,141,408 B2 | 11/2006 | Galen |

FOREIGN PATENT DOCUMENTS

WO    WO-2011/039382 A1    4/2011

OTHER PUBLICATIONS

Sakinc et al. (FEMS Microbiology Letters, 237:157-161, 2004).*
Henestrosa et al.: "Identification of additional genes belonging to the LexA regulon in *Escherichia coli*", Molecular Microbiology, Wiley-Blackwell Publishing Ltd, GB, vol. 35, No. 6, 1560-1572, Mar. 2000.
Wu et al.: "Temperature and Growth Rate Effects on the *hok/sok* Killer Locus for Enhanced Plasmid stability", Biotechnology Progress, American Institute of chemical engineers, US, vol. 10, No. 6. 621-629, Nov. 1994.
Fozo et al.: "Small toxic proteins and the antisense RNAs that repress them", Microbiology and Molecular Biology Reviews vol. 72, No, 4, 579-589, Dec. 2008.
ID: DINQ-ECOUT YNIPROT Dec. 4, 2007 (XP-002554070).

* cited by examiner

*Primary Examiner* — Brian J Gangle
(74) *Attorney, Agent, or Firm* — Locke Lord LLP; Gabriel J. McCool

(57) ABSTRACT

The present invention relates to the use of a dinQ-sRNA type I toxin-antitoxin systems for plasmid maintenance. An embodiment of the present invention relates to the use of the dinQ-sRNA type I toxin-antitoxin system for the manufacture of a plasmid selection system. In another embodiment of the present invention is the sRNA selected from the group consisting of agrA and agrB. Aspects of the present invention also relates to medical uses of the plasmid selection system.

5 Claims, 10 Drawing Sheets

Figure 1:
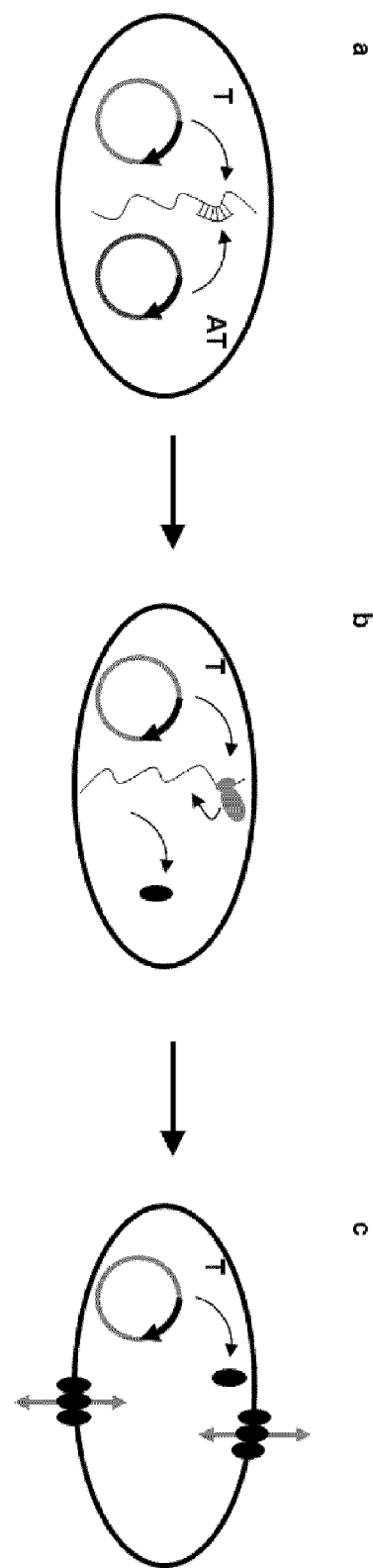
Figure 2:
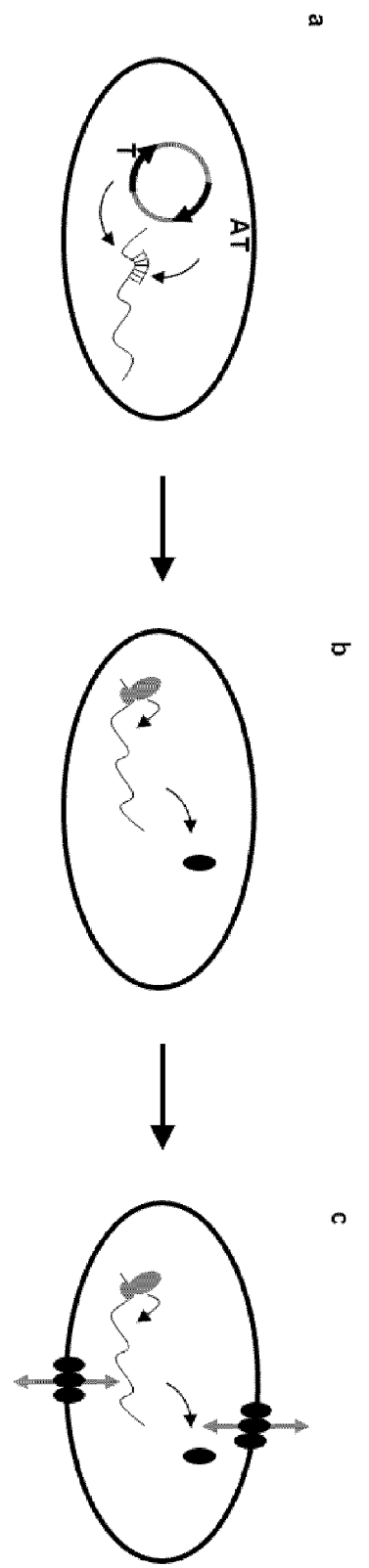

Stability of pBK446 (expresses agrB from its natural promoter) in BK4043 (a knockout of agrB that results in an over expression of dinQ) in both rich media (LB) and minimal media (M9, glucose) with either no selection (number of colonies ■, number of amp^R colonies □) or 0.5 (▲, Δ), 1 (●, o) & 2 (x, +) μg/ml Nalidixic acid. A positive control using ampicillin selection was also included (♦, ◊).

Stability of pBK440 (expresses the entire dinQ region including agrAB) in AB1157 in both rich media (LB) and minimal media (M9, glucose) with either no selection (number of colonies ■, number of amp$^R$ colonies □) or 0.5 (▲, △), 1 (•, o) & 2 (x, +) μg/ml Nalidixic acid. A positive control using ampicillin selection was also included (♦, ◊).

Stability of pBK440 (expresses the entire dinQ region including agrAB) in AB1157 in both rich media (LB) and minimal media (M9, glucose) with either no selection (number of colonies ■, number of amp^R colonies □) or 0.5 (▲, △), 1 (●, o) & 2 (x, +) μg/ml Nalidixic acid. A positive control using ampicillin selection was also included (♦, ◊).

SEQUENCE LISTING

<160> NUMBER OF SEQ ID NOS: 27

<210> SEQ ID NO 1
<211> LENGTH: 378
<212> TYPE: DNA
<213> ORGANISM: Escherichia coli

<400> SEQUENCE: 1
ggacgtgctg gttttataac ctgcatgtac tgtatgatta tccagttagc tctgaggcat       60
tttcactctg gcaatgcgca taaacgcttt caaagtcctg gtcagaagta cgggtggtgc      120
cgttaactga tgctctggcc ggagtgagag agttcttatc taacaatgag acatgcgccg      180
tgacaggcag tggatgagta agcggatgca ttctcactcc atcgcatgga gaaaacgggt      240
gattgataaa gcaatcatcg ttctaggggc gttaattgcg ctgctggaac tgatccgctt      300
tctgcttcag cttctgaact gatagcggaa acgtaattaa gggctaagag cacactactc      360
ttagcccttt aacattta                                                    378

<210> SEQ ID NO 2
<211> LENGTH: 57

```
<212> TYPE: DNA
<213> ORGANISM: Escherichia coli

<400> SEQUENCE: 2
atgcgcataa acgctttcaa agtcctggtc agaagtacgg gtggtgccgt taactga       57

<210> SEQ ID NO 3
<211> LENGTH: 18
<212> TYPE: PRT
<213> ORGANISM: Escherichia coli

<400> SEQUENCE: 3

Met Arg Ile Asn Ala Phe Lys Val Leu Val Arg Ser Thr Gly Gly Ala
1               5                   10                  15

Val Asn

<210> SEQ ID NO 4
<211> LENGTH: 150
<212> TYPE: DNA
<213> ORGANISM: Escherichia coli

<400> SEQUENCE: 4
atgcgccgtg acaggcagtg gatgagtaag cggatgcatt ctcactccat cgcatggaga      60
aaacgggtga ttgataaagc aatcatcgtt ctaggggcgt taattgcgct gctggaactg     120
atccgctttc tgcttcagct tctgaactga                                      150

<210> SEQ ID NO 5
<211> LENGTH: 49
<212> TYPE: PRT
<213> ORGANISM: Escherichia coli

<400> SEQUENCE: 5

Met Arg Arg Asp Arg Gln Trp Met Ser Lys Arg Met His Ser His Ser
1               5                   10                  15

Ile Ala Trp Arg Lys Arg Val Ile Asp Lys Ala Ile Ile Val Leu Gly
            20                  25                  30

Ala Leu Ile Ala Leu Leu Glu Leu Ile Arg Phe Leu Leu Gln Leu Leu
        35                  40                  45

Asn

<210> SEQ ID NO 6
<211> LENGTH: 129
<212> TYPE: DNA
<213> ORGANISM: Escherichia coli

<400> SEQUENCE: 6
atgagtaagc ggatgcattc tcactccatc gcatggagaa acgggtgat tgataaagca       60 atcatcgttc taggggcgtt aattgcgctg ctggaactga tccgctttct gcttcagctt     120
ctgaactga                                                             129

<210> SEQ ID NO 7
<211> LENGTH: 42
<212> TYPE: PRT
<213> ORGANISM: Escherichia coli

<400> SEQUENCE: 7

Met Ser Lys Arg Met His Ser His Ser Ile Ala Trp Arg Lys Arg Val
1               5                   10                  15

Ile Asp Lys Ala Ile Ile Val Leu Gly Ala Leu Ile Ala Leu Leu Glu
```

Leu Ile Arg Phe Leu Leu Gln Leu Leu Asn
        35                  40

<210> SEQ ID NO 8
<211> LENGTH: 117
<212> TYPE: DNA
<213> ORGANISM: Escherichia coli

<400> SEQUENCE: 8
atgcattctc actccatcgc atggagaaaa cgggtgattg ataaagcaat catcgttcta    60
ggggcgttaa ttgcgctgct ggaactgatc cgctttctgc ttcagcttct gaactga      117

<210> SEQ ID NO 9
<211> LENGTH: 38
<212> TYPE: PRT
<213> ORGANISM: Escherichia coli

<400> SEQUENCE: 9

Met His Ser His Ser Ile Ala Trp Arg Lys Arg Val Ile Asp Lys Ala
1               5                   10                  15

Ile Ile Val Leu Gly Ala Leu Ile Ala Leu Leu Glu Leu Ile Arg Phe
            20                  25                  30

Leu Leu Gln Leu Leu Asn
        35

<210> SEQ ID NO 10
<211> LENGTH: 84
<212> TYPE: DNA
<213> ORGANISM: Escherichia coli

<400> SEQUENCE: 10
gtgattgata aagcaatcat cgttctaggg gcgttaattg cgctgctgga actgatccgc    60
tttctgcttc agcttctgaa ctga                                          84

<210> SEQ ID NO 11
<211> LENGTH: 27
<212> TYPE: PRT
<213> ORGANISM: Escherichia coli

<400> SEQUENCE: 11

Val Ile Asp Lys Ala Ile Ile Val Leu Gly Ala Leu Ile Ala Leu Leu
1               5                   10                  15

Glu Leu Ile Arg Phe Leu Leu Gln Leu Leu Asn
            20                  25

<210> SEQ ID NO 12
<211> LENGTH: 85
<212> TYPE: DNA
<213> ORGANISM: Escherichia coli

<400> SEQUENCE: 12
gttagatgat ggctatctca ctccagtcag agccaccaac tcagggctgg aaagtaaaaa    60
accgacgcaa agtcggtttt tttac                                         85

<210> SEQ ID NO 13
<211> LENGTH: 86
<212> TYPE: DNA
<213> ORGANISM: Escherichia coli

<400> SEQUENCE: 13
tgttagataa gaactctctc actccagcca gagccaccaa ctcagggctg gaaagtaaaa    60
aaccgacgca aagtcggttt ttttac    86

<210> SEQ ID NO 14
<211> LENGTH: 330
<212> TYPE: DNA
<213> ORGANISM: Escherichia coli

<400> SEQUENCE: 14
ttagctctga ggcattttca ctctggcaat gcgcataaac gctttcaaag tcctggtcag    60
aagtacgggt ggtgccgtta actgatgctc tggccggagt gagagagttc ttatctaaca   120
atgagacatg cgccgtgaca ggcagtggat gagtaagcgg atgcattctc actccatcgc   180
atggagaaaa cgggtgattg ataaagcaat catcgttcta ggggcgttaa ttgcgctgct   240
ggaactgatc cgctttctgc ttcagcttct gaactgatag cggaaacgta attaagggct   300
aagagcacac tactcttagc cctttaacat   330

<210> SEQ ID NO 15
<211> LENGTH: 287
<212> TYPE: DNA
<213> ORGANISM: Escherichia coli

<400> SEQUENCE: 15
ttcaaagtcc tggtcagaag tacgggtggt gccgttaact gatgctctgg ccggagtgag    60
agagttctta tctaacaatg agacatgcgc cgtgacaggc agtggatgag taagcggatg   120
cattctcact ccatcgcatg gagaaaacgg gtgattgata aagcaatcat cgttctaggg   180
gcgttaattg cgctgctgga actgatccgc tttctgcttc agcttctgaa ctgatagcgg   240
aaacgtaatt aagggctaag agcacactac tcttagccct taacat   287

<210> SEQ ID NO 16
<211> LENGTH: 209
<212> TYPE: DNA
<213> ORGANISM: Escherichia coli

<400> SEQUENCE: 16
tgagacatgc gccgtgacag gcagtggatg agtaagcgga tgcattctca ctccatcgca    60
tggagaaaac gggtgattga taaagcaatc atcgttctag gggcgttaat tgcgctgctg   120
gaactgatcc gctttctgct tcagcttctg aactgatagc ggaaacgtaa ttaagggcta   180
agagcacact actcttagcc ctttaacat   209

<210> SEQ ID NO 17
<211> LENGTH: 27
<212> TYPE: PRT
<213> ORGANISM: Escherichia coli

<400> SEQUENCE: 17

Met Ile Asp Lys Ala Ile Ile Val Leu Gly Ala Leu Ile Ala Leu Leu
1               5                   10                  15

Glu Leu Ile Arg Phe Leu Leu Gln Leu Leu Asn
            20                  25

<210> SEQ ID NO 18
<211> LENGTH: 3094
<212> TYPE: DNA
<213> ORGANISM: Artificial Sequence
<220> FEATURE:

<223> OTHER INFORMATION: plasmid cloning vector

<400> SEQUENCE: 18

```
agcttccaca cattatattg ttatccgctc acaatgtcaa ttggaaattt aaaataattt      60
tctgaggatc cactagttct agagcggccg ccaccgcggt ggctgcatta atgaatcggc     120
caacgcgcgg ggagaggcgg tttgcgtatt gggcgctctt ccgcttcctc gctcactgac     180
tcgctgcgct cggtcgttcg gctgcggcga gcggtatcag ctcactcaaa ggcggtaata     240
cggttatcca cagaatcagg ggataacgca ggaaagaaca tgtgagcaaa aggccagcaa     300
aaggccagga accgtaaaaa ggccgcgttg ctggcgtttt tccataggct ccgcccccct     360
gacgagcatc acaaaaatcg acgctcaagt cagaggtggc gaaacccgac aggactataa     420
agataccagg cgtttccccc tggaagctcc ctcgtgcgct ctcctgttcc gaccctgccg     480
cttaccggat acctgtccgc ctttctccct tcgggaagcg tggcgctttc tcatagctca     540
cgctgtaggt atctcagttc ggtgtaggtc gttcgctcca agctgggctg tgtgcacgaa     600
ccccccgttc agcccgaccg ctgcgcctta tccggtaact atcgtcttga gtccaacccg     660
gtaagacacg acttatcgcc actggcagca gccactggta acaggattag cagagcgagg     720
tatgtaggcg gtgctacaga gttcttgaag tggtggccta actacggcta cactagaagg     780
acagtatttg gtatctgcgc tctgctgaag ccagttacct tcggaaaaag agttggtagc     840
tcttgatccg gcaaacaaac caccgctggt agcggtggtt tttttgtttg caagcagcag     900
attacgcgca gaaaaaaagg atctcaagaa gatcctttga tcttttctac ggggtctgac     960
gctcagtgga acgaaaactc acgttaaggg attttggtca tgagattatc aaaaaggatc    1020
ttcacctaga tccttttaaa ttaaaaatga agttttaaat caatctaaag tatatatgag    1080
taaacttggt ctgacagtta ccaatgctta atcagtgagg cacctatctc agcgatctgt    1140
ctatttcgtt catccatagt tgcctgactc cccgtcgtgt agataactac gatacgggag    1200
ggcttaccat ctggccccag tgctgcaatg ataccgcgag acccacgctc accggctcca    1260
gatttatcag caataaacca gccagccgga agggccgagc gcagaagtgg tcctgcaact    1320
ttatccgcct ccatccagtc tattaattgt tgccgggaag ctagagtaag tagttcgcca    1380
gttaatagtt tgcgcaacgt tgttgccatt gctacaggca tcgtggtgtc acgctcgtcg    1440
tttggtatgg cttcattcag ctccggttcc caacgatcaa ggcgagttac atgatccccc    1500
atgttgtgca aaaaagcggt tagctccttc ggtcctccga tcgttgtcag aagtaagttg    1560
gccgcagtgt tatcactcat ggttatggca gcactgcata attctcttac tgtcatgcca    1620
tccgtaagat gcttttctgt gactggtgag tactcaacca agtcattctg agaatagtgt    1680
atgcggcgac cgagttgctc ttgcccggcg tcaatacggg ataataccgc gccacatagc    1740
agaactttaa aagtgctcat cattggaaaa cgttcttcgg ggcgaaaact ctcaaggatc    1800
ttaccgctgt tgagatccag ttcgatgtaa cccactcgtg cacccaactg atcttcagca    1860
tcttttactt tcaccagcgt ttctgggtga gcaaaaacag gaaggcaaaa tgccgcaaaa    1920
aagggaataa gggcgacacg gaaatgttga atactcatac tcttcctttt tcaatattat    1980
tgaagcattt atcagggtta ttgtctcatg agcggataca tatttgaatg tatttagaaa    2040
aataaacaaa taggggttcc gcgcacattt ccccgaaaag tgccacctaa attgtaagcg    2100
ttaatatttt gttaaaattc gcgttaaatt tttgttaaat cagctcattt tttaaccaat    2160
aggccgaaat cggcaaaatc ccttataaat caaaagaata gaccgagata gggttgagtg    2220
ttgttccagt ttggaacaag agtccactat taaagaacgt ggactccaac gtcaaagggc    2280
```

-continued

```
gaaaaaccgt ctatcagggc gatggcccac tacgtgaacc atcaccctaa tcaagttttt      2340
tggggtcgag gtgccgtaaa gcactaaatc ggaaccctaa agggagcccc cgatttagag      2400
cttgacgggg aaagccggcg aacgtggcga aaaggaagg gaagaaagcg aaaggagcgg       2460
gcgctagggc gctggcaagt gtagcggtca cgctgcgcgt aaccaccaca cccgccgcgc      2520
ttaatgcgcc gctacagggc gcgtcccatt cgccattcag gctgcgcaac tgttgggaag     2580
ggcgatcggt gcgggcctct tcgctattac gccagctggc gaaagggga tgtgctgcaa     2640 ggcgattaag ttgggtaacg ccagggtttt cccagtcacg acgttgtaaa acgacggcca    2700
gtgagcgcgc gtaatacgac tcactatagg gcgaattggg taccgggccc ccctcgacg     2760 cgtaaaaaaa cccgccgggg cgggttttt tacgcgtcga ggaagtgccg gatccgaaaa      2820
gaagaactaa ctcgttgtgg agaataacaa aaatggtcat ctggagctta caggtggcca    2880
ttcgtgggac agtatccctg acagcctaca aaacgcaatt gaagaacgcg aggcatcgtc    2940
ttaacgaggc accgaggcgt cgcattcttc agatggttca acccttaagc ggatcctcag    3000
ttcagaagct gaagcagaaa gcggatcagt tccagcagcg caattaacgc ccctagaacg    3060
atgattgctt tatcaaccat ccgttttcct ccta                                3094
```

<210> SEQ ID NO 19
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 19

Met Ile Asp Lys Ala Ile Ile Val Leu Lys Ala Leu Ile Ala Leu Leu
1               5                   10                  15

Glu Leu Ile Arg Phe Leu Leu Gln Leu Leu Asn
            20                  25

<210> SEQ ID NO 20
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 20

Met Ile Asp Lys Ala Ile Ile Val Leu Gly Ala Leu Ile Ala Leu Leu
1               5                   10                  15

Glu Leu Ile Arg Phe Leu Ile Gln Leu Leu Asn
            20                  25

<210> SEQ ID NO 21
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 21

Met Ile Asp Lys Ala Ile Val Val Leu Gly Ala Leu Ile Ala Leu Leu
1               5                   10                  15

Glu Leu Ile Arg Phe Leu Leu Gln Leu Leu Asn
            20                  25

<210> SEQ ID NO 22
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 22

Met Ile Asp Lys Ala Ile Ile Val Leu Gly Ala Ile Val Ala Leu Leu
1               5                   10                  15

Glu Leu Ile Arg Phe Leu Leu Gln Leu Leu Asn
            20                  25

<210> SEQ ID NO 23
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 23

Met Ile Asp Lys Ala Ile Ile Val Leu Asn Ala Leu Ile Ala Leu Leu
1               5                   10                  15

Glu Leu Ile Arg Phe Leu Leu Gln Leu Leu Asn
            20                  25

<210> SEQ ID NO 24
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 24

Met Ile Arg Lys Ala Ile Ile Val Leu Gly Ala Leu Ile Ala Leu Leu
1               5                   10                  15

Glu Leu Ile Arg Phe Leu Leu Gln Leu Leu Asn
            20                  25

<210> SEQ ID NO 25
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 25

Met Ile Asp Lys Ala Ile Ile Val Leu Gly Ala Leu Ile Ala Val Leu
1               5                   10                  15

Glu Leu Ile Arg Phe Leu Leu Gln Leu Leu Asn
            20                  25

<210> SEQ ID NO 26
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 26

```
Met Ile Asp Lys Ala Ile Ile Val Leu Gly Ala Leu Ile Ala Leu Leu
1               5                   10                  15

Glu Leu Val Arg Phe Leu Leu Gln Leu Leu Asn
                20                  25

<210> SEQ ID NO 27
<211> LENGTH: 27
<212> TYPE: PRT
<213> ORGANISM: Artificial Sequence
<220> FEATURE:
<223> OTHER INFORMATION: synthesized peptide originating from
      Escherichia coli

<400> SEQUENCE: 27

Met Ile Asp Lys Ala Ile Ile Val Leu Gly Ala Leu Ile Ala Leu Leu
1               5                   10                  15

Glu Leu Ile Arg Phe Ile Leu Gln Leu Leu Asn
                20                  25
```

DINQ-SRNA TYPE I TOXIN-ANTITOXIN SYSTEM FOR PLASMID MAINTENANCE

CROSS-REFERENCE TO RELATED APPLICATIONS

This application is the national phase under 35 U.S.C. §371 of PCT International Application No. PCT/EP2011/070852, filed Nov. 23, 2011, which claims the benefit of EP Patent Application No. 10192306.8, filed Nov. 23, 2010, the entire contents of the aforementioned applications are hereby incorporated herein by reference.

BACKGROUND FOR THE INVENTION

Plasmids found in the natural environment have various systems to enable their maintenance in bacteria and propagation between bacteria.

During the process of adapting plasmids for synthetic use various functions were removed such as those responsible for propagation, otherwise referred to as mobilization elements so as to improve their safety profile.

Additionally elements that enabled maintenance were removed.

Upon finding that the synthetic cloning vectors were unstable antibiotic resistance genes were inserted and used in combination with antibiotics for the selection and maintenance of the plasmids.

Bacteria that lose the plasmid during cell division are killed by the antibiotic whilst those that retain the plasmid express proteins capable of negating the lethal effects of the antibiotic.

The success of this strategy now means that practically all synthetic plasmids in use today contain antibiotic resistance genes.

Recent attempts to increase the biosafety profile of plasmid based therapies have included genetically attenuating vectors so that they have a reduced ability to persist in the host.

This reduction in persistence results in an inability to transfer genetic information.

Earlier studies indicated that synthetic plasmids were not liable to transfer to the natural bacterial population.

However, more recent work has demonstrated that transmission may be possible in the environment of the intestinal tract.

The spread of antibiotic resistance in gram negative bacteria has also been acknowledged to be mostly due to the transfer of plasmids that contain antibiotic resistance genes.

With sufficient numbers of host and recipient bacteria present in the human intestinal tract transfer of self-transmissible plasmids occurs both with and without selection.

The rate of transformation of plasmids has even been shown to be higher in vivo than that can be achieved in vitro.

Non-mobilizable plasmids can in fact be transferred from one bacterium to another in the presence of another, conjugative, plasmid. This even applies if the conjugative plasmid is present in the recipient bacterium.

Many plasmid selection systems today are based on the use of antibiotics and genes that express proteins capable of negating the lethal effects of the antibiotic.

It may be advantageous for example to not to have to use an antibiotic resistance gene in a plasmid due to its inclusion in the plasmid, which may be used in antibiotic treatment or vaccine production.

The use of plasmids in transgenic crops where the antibiotic resistance genes may survive into the intestinal systems of livestock has been brought into question.

In addition the FDA actively discourages the use of antibiotic resistance genes in recombinant plasmid based therapies in order to avoid the accidental release of these genes into the environmental gene pool.

Recombinant plasmid based therapies include but are not limited to gene therapy and recombinant bacteriophage therapy.

In addition the emergence of antibiotic resistant bacteria poses a serious threat. Toxin-antitoxin (TA) systems otherwise known as toxin-antidote (TA) or post-segregational killing (PSK) systems can be found either encoded on plasmids or chromosomally.

They are divided into two broadly distinguishable classes, type I and type II.

Type I encode a small hydrophobic toxic peptide that acts by disrupting membrane function and normally a single antisense sRNA antitoxin. An example of this is the chromosomally encoded dinQ-agrB system. Some type I systems such as the plasmid encoded hok-sok system also contain a second regulatory sRNA.

Type II systems are those in which both the toxin and antitoxin are proteins and the toxin often acts through affecting intracellular activity.

Recently, a third type of TA loci was identified. In this case, the antitoxin is a small cis-encoded RNA that inhibits toxin activity by direct molecular interaction.

The functions of chromosomally encoded TA systems are likely to be quite diverse, depending on the type of TA system, their genomic location and their host species. Plasmid encoded TA systems are required for plasmid replication and maintenance.

SUMMARY

The present invention relates to a plasmid selection system comprising a dinQ-sRNA type I toxin-antitoxin system.

In one embodiment of the present invention is the sRNA selected from agrA and agrB.

In one embodiment of the present invention the toxin and the antitoxin are comprised in different plasmids.

In another embodiment of the present invention the toxin and the antitoxin are comprised in the same plasmid.

In yet another embodiment of the present invention the toxin is comprised in a bacterial chromosome.

Another aspect of the present invention relates to the use of a type I toxin-antitoxin system for the manufacture of a plasmid selection system.

Another aspect of the present invention relates to one or more nucleic acids encoding the plasmid selection system of the present invention.

Other aspects of the present invention include medical applications of the present invention including medical uses and treatments such as the treatment of a bacterial infection.

FIGURE LEGENDS

FIG. 1

How a toxin(T)-antitoxin(AT) system operates during plasmid maintenance.

a. An mRNA with the potential to be translated into a toxin is transcribed, either from a plasmid, or chromosomally. Before this primary transcript can be processed into the active secondary transcript it interacts with the sRNA resulting in an alternative inactive secondary transcript. This interaction enables the persistence of the plasmid within the bacterial population.

b. Loss of the plasmid encoding the antitoxin and after the degradation of residual antitoxin sRNA will allow the primary transcript from the toxin to be processed into a form, the active form, that allows for the translation of the toxic peptide.
c. The build up of the toxin in the cell membrane results in the disruption of the membrane, depolarization and loss of viability.

FIG. 2

A single plasmid toxin(T)-antitoxin(AT) system.
a. The potentially toxin generating mRNA and sRNA are generated from the same plasmid however they have substantially different stabilities. The antitoxin sRNA binds to the mRNA of the toxin and cause it to be processed in such a way that no toxin can be translated.
b. Following loss of the plasmid the sRNA is rapidly degraded leaving only the mRNA of the toxin present which can then be processed into a transcript which can be translated to produce the toxin.
c. The toxin exerts its toxic effect in the inner membrane of the bacterium causing membrane depolarization and as a consequence loss of viability.

FIG. 3

An overview of the proposed repressor plasmid containing and following elements: 2× lacIq for repression of lad operators, 1× tetracycline repressor for repression of corresponding operator sequence, an origin of replication, antibiotic resistance gene and the dinQ toxin encoding region. This plasmid will therefore repress expression from lad and tetracycline repressor operators and in addition produce the mRNA for DinQ which has the potential to be regulated by agrB and in failing this produce the DinQ toxin.

FIG. 4

An overview of the phagemid, f1(+), encoding the antibacterial toxin under the control of a tetracycline repressor operator. The stability of the plasmid will be maintained by the sRNA antitoxin agrB.

FIG. 5

Figure 5:
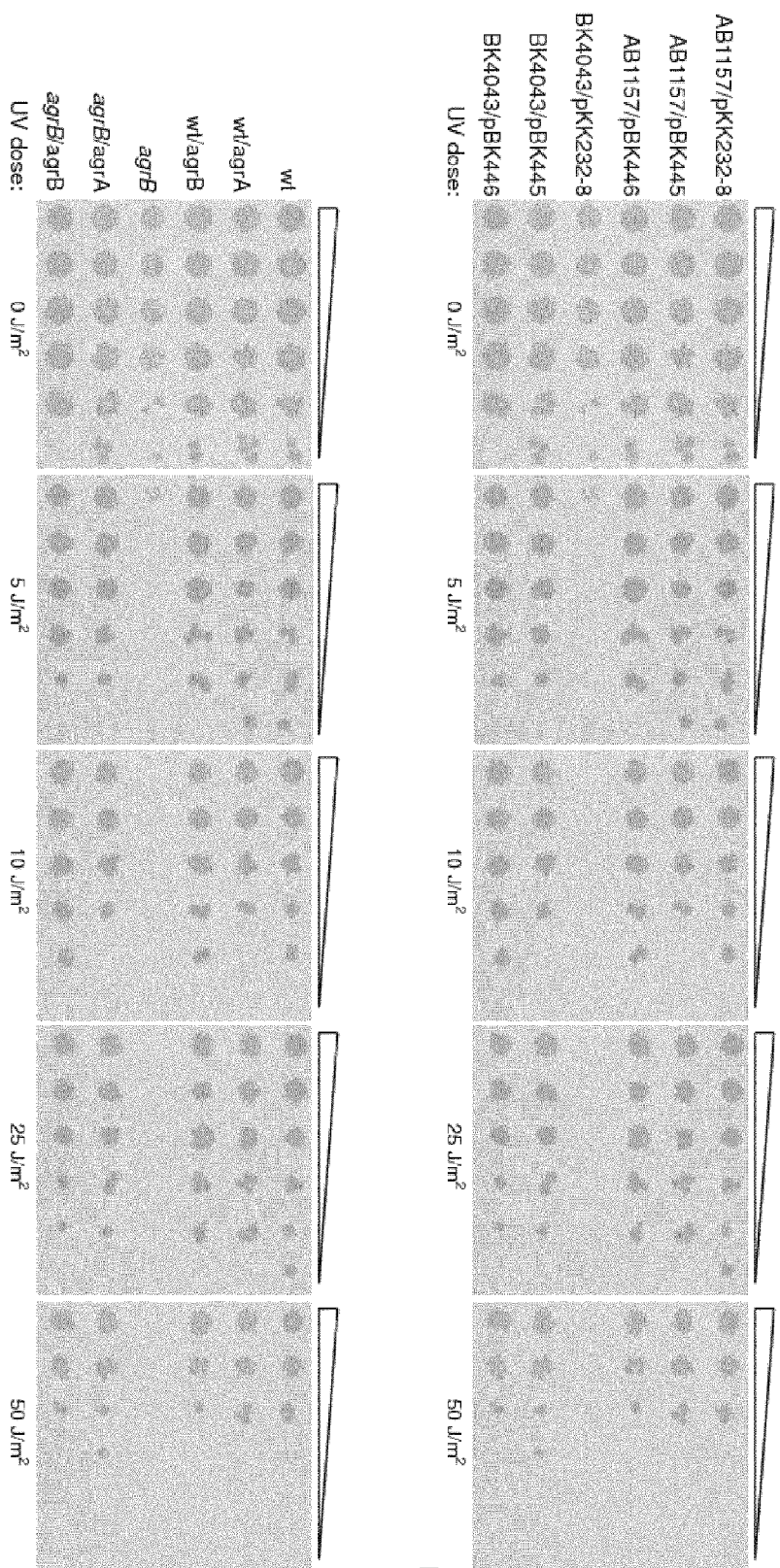

The two panels of FIG. 5 use the same data, the difference being the notation which is explained below. The rows of bacterial spots represent a 10-fold dilution series where the spots from left to right in each row in each grey box represent a 10-fold dilution of the previous spot to the left. The spots with the highest bacterial concentrations, therefore, are the ones on the left of each row in each grey square. This also means that the spots furthest to the right represent a 1/100 000 dilution of the original spot. From top to bottom of each square are six strains.

FIG. 6

The removal of the antitoxin agrB following recombination results in fewer transformants due to the induction in translation of dinQ.

FIG. 7

The expression of a agrB expressing plasmid stabilises the strain BK4043 in both rich media (LB) and minimal media (M9 glucose).

FIG. 8

The plasmid expression of the entire dinQ locus including regulatory sRNAs agrA & agrB results in the stable maintenance of the plasmid in AB1157.

FIG. 9

The plasmid expression of the entire dinQ locus including regulatory sRNAs agrA & agrB results in the stable maintenance of the plasmid in MG1655.

FIG. 10

Instability of pBK444 in MG1655, example of a toxic construct in both LB and minimal media+glucose with either no selection or 1 & 2 μg/ml Nalidixic acid.

DETAILED DESCRIPTION

The present invention relates to a vector selection system comprising a dinQ-sRNA type I toxin-antitoxin system.

In one embodiment of the present invention the vector is a plasmid.

In another embodiment of the present invention is the sRNA selected from the group consisting of agrA and agrB.

Selection Marker

A vector selection system is a system comprising a selection marker. A selection marker is a gene carried on a vector that ensures that it is passed onto the next generation of bacteria. It is combined with a toxic moiety that ensures that any progeny that do not contain the plasmid are eliminated. Selection is necessary as bacteria without plasmids, particularly high copy plasmids have a significant growth advantage and would otherwise quickly dominate a bacterial population under exponential growth.

Vector

The term "vector" refers to a DNA molecule used as a vehicle to transfer recombinant genetic material into a host cell. The four major types of vectors are plasmids, bacteriophages and other viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences. Simpler vectors called transcription vectors are only capable of being transcribed but not translated: they can be replicated in a target cell but not expressed, unlike expression vectors. Transcription vectors are used to amplify the inserted heterologous sequences. The transcripts may subsequently be isolated and used as templates suitable for in vitro translation systems. The choice of vector employed in embodiments of the present invention depends on the specific application of the vector encoding the polypeptides or polynucleotide of the invention.

In an embodiment of the present invention is the vector a plasmid and the vector selection system a plasmid selection system.

Thus relates a plasmid selection system to at least one plasmid that comprises the toxin and/or antitoxin in accordance with the above description.

Phagemid and Bacteriophage

A phagemid or phasmid is a type of cloning vector developed as a hybrid of the filamentous phage M13 and plasmids to produce a vector that can grow as a plasmid, and also be packaged as single stranded DNA in viral particles.

Phagemids contain an origin of replication (ori) for double stranded replication, as well as an f1 on to enable single stranded replication and packaging into phage particles.

Many commonly used plasmids contain an f1 on and are thus phagemids. Similarly to a plasmid, a phagemid can be used to clone DNA fragments and be introduced into a bacterial host by a range of techniques (transformation, electroporation).

However, infection of a bacterial host containing a phagemid with a 'helper' phage, for example VCSM13 or M13K07, provides the necessary viral components to enable single stranded DNA replication and packaging of the phagemid DNA into bacteriophage particles. These are secreted through the cell wall and released into the medium.

In the present context is the term phagemid is defined as a bacteriophage whose genome contains a plasmid that can be excised by co-infection of the host with a helper phage.

A bacteriophage is defined as any one of a number of viruses that infect bacteria.

They do this by injecting genetic material, which they carry enclosed in an outer protein capsid. The genetic material can be ssRNA, dsRNA, ssDNA, or dsDNA ('ss-' or 'ds-' prefix denotes single-strand or double-strand) along with either circular or linear arrangement.

An aspect of the present invention relates to a phagemid comprising agrA or agrB.

Another aspect of the present invention relates to a phagemid comprising dinQ.

Another aspect of the present invention relates to a phagemid comprising dinQ, agrA and agrB.

Yet another aspect of the present invention relates to a bacteriophage comprising the phagemid of the present invention.

One application of bacteriophages is as a possible therapy against multi-drug-resistant strains of many bacteria.

Another application of bacteriophages is phage therapy, which is the therapeutic use of bacteriophages to treat pathogenic bacterial infections.

Bacteria

Bacteriophages infect bacteria and they have been investigated as a potential means to eliminate pathogens like *Campylobacter* in raw food and *Listeria* in fresh food or to reduce food spoilage bacteria.

In agricultural practice phages were used to fight pathogens like *Campylobacter, Escherichia* and *Salmonella* in farm animals, *Lactococcus* and *Vibrio* pathogens in fish from aquaculture and *Erwinia* and *Xanthomonas* in plants of agricultural importance.

Recently the phage therapy approach has been applied to systemic and even intracellular infections and the addition of non-replicating phage and isolated phage enzymes like lysins to the antimicrobial arsenal.

Bacteriophage treatment offers a possible alternative to conventional antibiotic treatments for bacterial infection.

Bacteria infected by the bacteriophages are gram-negative bacteria or gram-positive bacteria.

In a preferred embodiment of the present invention are the bacteria infected by the bacteriophages of the present invention gram-negative bacteria.

The pathogenic capability of Gram-negative bacteria is often associated with certain components of Gram-negative cell walls, in particular, the lipopolysaccharide layer (also known as LPS or endotoxin layer—a component of the outer membrane).

In humans, LPS triggers an innate immune response characterized by cytokine production and immune system activation.

Inflammation is a common result of cytokine production, which can also produce host toxicity.

The proteobacteria are a major group of Gram-negative bacteria, including *Escherichia coli* (*E. coli*), *Salmonella, Shigella*, and other Enterobacteriaceae, *Pseudomonas, Moraxella, Helicobacter, Stenotrophomonas, Bdellovibrio*, acetic acid bacteria, *Legionella* and numerous others.

Other notable groups of Gram-negative bacteria include the cyanobacteria, spirochaetes, green sulfur and green non-sulfur bacteria.

Medically relevant Gram-negative cocci include three organisms, which cause a sexually transmitted disease (*Neisseria gonorrhoeae*), a meningitis (*Neisseria meningitidis*), and respiratory symptoms (*Moraxella catarrhalis*).

Medically relevant Gram-negative bacilli include a multitude of species. Some of them primarily cause respiratory problems (*Hemophilus influenzae, Klebsiella pneumoniae, Legionella pneumophila, Pseudomonas aeruginosa*), primarily urinary problems (*Escherichia coli, Proteus mirabilis, Enterobacter cloacae, Serratia marcescens*), and primarily gastrointestinal problems (*Helicobacter pylori, Salmonella enteritidis, Salmonella typhi*).

Gram-negative bacteria associated with nosocomial infections include *Acinetobacter baumannii*, which cause bacteremia, secondary meningitis, and ventilator-associated pneumonia in intensive-care units of hospital establishments.

Bacteriophages also infect gram-positive bacteria.

In the classical sense, six Gram-positive genera are typically pathogenic in humans.

Two of these, *Streptococcus* and *Staphylococcus*, are cocci (sphere-shaped bacteria). The remaining organisms are bacilli (rod-shaped bacteria) and can be subdivided based on their ability to form spores. The non-spore formers are *Corynebacterium* and *Listeria* (a coccobacillus), whereas *Bacillus* and *Clostridium* produce spores. The spore-forming bacteria can again be divided based on their respiration: *Bacillus* is a facultative anaerobe, while *Clostridium* is an obligate anaerobe.

Thus, an aspect of the present invention relates to a phagemid of the present invention for use in the treatment of a bacterial infection in an animal or a mammal caused by gram-negative bacteria or gram-positive bacteria.

Another aspect of the present invention relates to a bacteriophage of the present invention for use in the treatment of a bacterial infection in an animal or a mammal caused by gram-negative bacteria or gram-positive bacteria.

In an embodiment of the present invention are the bacteria multi-resistant bacteria.

In an embodiment of the present invention is the mammal a human.

In another embodiment of the present invention is the mammal chosen from the list consisting of a cow, a pig, a horse, a sheep, a dog or a cat.

In yet another embodiment of the present invention is the animal poultry such as a chicken.

In yet another embodiment of the present invention is the animal a bird.

Another aspect of the present invention relates to phagemid or bacteriophage of the present invention for use in the treatment of sepsis.

An embodiment of the present invention relates to phagemid or bacteriophage of the present invention, wherein the phagemid or bacteriophage is for adjunctive treatment.

Another embodiment of the present invention relates to phagemid or bacteriophage of the present invention use as a medicament.

Another embodiment of the present invention relates to phagemid or bacteriophage of the present invention for use in the treatment of a bacterial infection.

Another embodiment of the present invention relates to phagemid or bacteriophage of the present invention for use in the treatment of sepsis.

Another embodiment of the present invention relates to phagemid or bacteriophage of the present invention for use in the treatment an infected wound.

Another embodiment of the present invention relates to a pharmaceutical composition comprising
  a bacteriophage according to the present invention, or
  an phagemid according to the present invention, and
  at least one pharmaceutically acceptable additive.

Toxin Effect

The extremely efficient toxin induces stasis or death in cells that lack the plasmid after cell division leading to stabilization of the plasmid. In most cases of type I TA systems, the protein toxin and RNA antitoxin are encoded on opposite strands, while all known type II TA systems are organized as operons with coupled translation.

The proteic antitoxin is usually encoded by the first gene and always acts as a transcriptional autorepressor of the operon, either alone or in a complex with the toxin molecule. Thus, antitoxins control toxin activity in two ways: through direct binding and through transcriptional regulation.

sRNA based repression occurs before the translation of the protein and will block translation of toxic proteins where even small amounts of the toxin can cause damage to the cell. By preventing translation, the cell does not expend energy in synthesizing the toxic proteins.

Additionally, the effects of the sRNA in a type I TA system are irreversible since the sRNA-mRNA interaction usually promotes cleavage of the mRNA.

Type II TA systems are on the other hand reversible since the antitoxin protein can dissociate from its corresponding toxin.

In one embodiment of the present invention the type I toxin-antitoxin system in the plasmid selection system is DinQ-agrB.

In another embodiment of the present invention the type I toxin-antitoxin system in the plasmid selection system is DinQ-agrA.

DinQ-sRNA

DinQ-sRNA is a type I toxin-antitoxin (TA) system, where the small RNA (sRNA) molecules agrA or agrB controls the translation of the hydrophobic inner membrane bound DinQ toxin by modulation of RNA processing of the DinQ primary transcript via its complementarities to the primary transcript and subsequent double stranded RNase activity.

By including the antitoxin moiety on the plasmid to be stably maintained within a bacterial strain and the toxin element on another plasmid, under e.g. antibiotic control, or within the genome of the bacteria under the control of an inducible promoter the system will remain in equilibrium.

Loss of the desired plasmid, however, and subsequent loss of agrA or agrB transcription and degradation of the agrA or agrB sRNA already present in the bacterium will lead to translation of the active DinQ peptide, which will then in turn exert its toxic effects on the cell membrane so killing the bacterium, post-segregational killing.

The whole TA system can also be based on one plasmid.

The temporal difference in half lives between the sRNA, antitoxin and the mRNA of the toxin, will lead to a dominance of the toxin mRNA over sRNA a short time after plasmid loss and so its alternative processing into a mRNA capable of translating the peptide toxin.

Thus, in another embodiment of the present invention, the antitoxin is agrA or agrB.

In one embodiment of the present invention, the toxin and the antitoxin are comprised in different plasmids.

In one embodiment of the present invention are the toxin and the antitoxin comprised in the same plasmid.

In yet another embodiment of the present invention the toxin is comprised in a bacterial chromosome.

Another aspect of the present invention relates to the use of a type I toxin-antitoxin system for the manufacture of a plasmid selection system.

Antibiotic Resistance

In the sense of the present invention antibiotic resistance refers to the ability of a bacteria to withstand the effects of an antibiotic. It is a specific type of drug resistance. Antibiotic resistance evolves naturally via natural selection acting upon random mutation, but it could also be engineered by applying an evolutionary stress on a population. Once such a gene is generated, bacteria can then transfer the genetic information in a horizontal fashion (between individuals) for example by plasmid exchange. Antibiotic resistance can also be introduced artificially into a bacteria through transformation protocols.

The Polypeptides of the Invention

In the context of the present invention "polypetides" and "peptides" are interchangeable terms in the context of the present invention.

The dinQ polypeptides are encoded by the dinQ transcripts, which contain two open reading frames (ORFs) encoding peptides of 18 and 49 amino acids (aa), in which the 49 aa ORF contain four potential start codons, ORF-II (or ORF-2) of 49 aa, ORF-III (or ORF-3) of 42 aa, ORF-IV (or ORF-4) of 38 aa and an alternative transcription start codon GTG at ORF-V (or ORF-5) of 27 aa. The inventors have only detected translation of ORF-V in vivo. None of the dinQ ORFs shows strong homology to any known peptides. Roman numerals and Arabic numerals are used interchangeably to refer to the specific ORFs of dinQ.

The dinQ transcripts encode toxic polypeptides of which one is particularly toxic, the dinQ ORF-V polypeptide (SEQ ID NO. 11). Cellular fractionation shows that the DinQ polypeptide peptide localized to the inner membrane, overexpression of the polypeptides caused depolarization of the bacterial cell membrane and decreased the intracellular ATP concentration.

The dinQ ORF-V polypeptide (SEQ ID NO. 11) can be manipulated without interfering with the toxicity. The manipulations include deletions, substitutions, eliminations and additions.

Examples of such manipulations can be seen in example 10.

Sequences that have been manipulated while retaining toxicity include the polypeptides selected from the group consisting of SEQ ID NO. 3, SEQ ID NO. 5, SEQ ID NO. 7, SEQ ID NO. 9, SEQ ID NO. 11, SEQ ID NO. 12, SEQ ID NO. 13, SEQ ID NO. 14, SEQ ID NO. 15, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26 and SEQ ID NO. 27.

Accordingly, in one embodiment of the present invention is the dinQ polypeptide selected from the group consisting of
(a) a polypeptide encoded by SEQ ID NO. 1 (dinQ gene sequence),
(b) a functionally equivalent subsequence of (a) of at least 15 amino acids
(c) a functionally equivalent polypeptide with a sequence identity of at least 85% to (a) or (b).

In one embodiment, said is dinQ polypeptide selected from the group consisting of SEQ ID NO. 3 (DinQ ORF-I peptide), SEQ ID NO. 5 (DinQ ORF-II peptide), SEQ ID NO. 7 (DinQ ORF-III peptide), SEQ ID NO. 9 (DinQ ORF-IV peptide), SEQ ID NO. 11(DinQ ORF-V peptide) and SEQ ID NO. 17 (DinQ ORF-V peptide with N-terminal Met).

In another embodiment the polypeptide is encoded by a polynucleotide sequence selected from the group consisting of SEQ ID NO. 14 (dinQ full length transcript, dinQ-a), SEQ ID NO. 15 (dinQ-b transcript), and SEQ ID NO. 16 (dinQ-d transcript).

In another embodiment, the functionally equivalent polypeptide is selected from the group consisting of SEQ ID NO. 19 (G10K variant of DinQ ORF-V peptide with N-terminal Met), SEQ ID NO. 20 (L23I variant of DinQ ORF-V peptide with N-terminal Met), SEQ ID NO. 21 (I7V variant of DinQ ORF-V peptide with N-terminal Met), SEQ ID NO. 22 (L12I, I13V double mutant variant of DinQ ORF-V peptide with N-terminal Met), SEQ ID NO. 23 (G10N variant of DinQ ORF-V peptide with N-terminal Met), SEQ ID NO. 24 (D3R variant of DinQ ORF-V peptide with N-terminal Met), SEQ ID NO. 25 (L15V variant of DinQ ORF-V peptide with N-terminal Met), SEQ ID NO. 26 (I19V variant of DinQ ORF-V peptide with N-terminal Met) and SEQ ID NO. 27 (L22I variant of DinQ ORF-V peptide with N-terminal Met).

In one embodiment, said antibacterial polypeptide has the amino acid sequence set forth in SEQ ID NO. 5 (DinQ ORF-II peptide).

In a preferred embodiment, has the dinQ polypeptide the amino acid sequence set forth in SEQ ID NO. 9 (DinQ ORF-IV peptide).

In another preferred embodiment, has the dinQ polypeptide the amino acid sequence set forth in SEQ ID NO. 11 (DinQ ORF-V peptide).

In a further embodiment, has the dinQ polypeptide the amino acid sequence set forth in SEQ ID NO. 17 (DinQ ORF-V peptide with N-terminal Met). The DinQ peptide set forth in SEQ ID NO. 17 is the form that results from the translation of the DinQ ORF-V using GUG as start codon. When GUG is used as start-codon, it is translated as methionine, although the codon normally encodes a Val. In the prokaryotic translation machinery a distinct tRNA is present that initiates such translation. The DinQ peptide set forth in SEQ ID NO. 17 is also referred to as the wild type DinQ ORF-V peptide herein.

In one embodiment, the dinQ polypeptide has the amino acid sequence set forth in SEQ ID NO. 19 (G10K variant of DinQ ORF-V peptide with N-terminal Met).

In another embodiment, the dinQ polypeptide has the amino acid sequence set forth in SEQ ID NO. 20 (L23I variant of DinQ ORF-V peptide with N-terminal Met).

In yet another embodiment, the dinQ polypeptide has the amino acid sequence set forth in SEQ ID NO. 21 (I7V variant of DinQ ORF-V peptide with N-terminal Met).

In a further embodiment, the dinQ polypeptide has the amino acid sequence set forth in SEQ ID NO. 22 (L12I, I13V double mutant variant of DinQ ORF-V peptide with N-terminal Met).

In a further embodiment, the dinQ polypeptide has the amino acid sequence set forth in SEQ ID NO. 23 (G10N variant of DinQ ORF-V peptide with N-terminal Met).

In a further embodiment, the dinQ polypeptide has the amino acid sequence set forth in SEQ ID NO. 24 (D3R variant of DinQ ORF-V peptide with N-terminal Met).

In a further embodiment, the dinQ polypeptide has the amino acid sequence set forth in SEQ ID NO. 25 (L15V variant of DinQ ORF-V peptide with N-terminal Met).

In a further embodiment, the dinQ polypeptide has the amino acid sequence set forth in SEQ ID NO. 26 (I19V variant of DinQ ORF-V peptide with N-terminal Met).

In a further embodiment, the dinQ polypeptide has the amino acid sequence set forth in SEQ ID NO. 27 (L22I variant of DinQ ORF-V peptide with N-terminal Met).

The antibacterial polypeptide of the invention may be in the form of isolated polypeptides such as polypeptides isolated from a suitable host adapted for recombinant expression of said polypeptides (biosynthesized). In another embodiment, the antibacterial polypeptides isolated from in vitro translation of polynucleotide encoding said polypeptide.

One embodiment of the present invention provide functionally equivalent subsequence of a polypeptide encoded by SEQ ID NO. 1 (dinQ gene sequence), said subsequence having at least the length of 15 amino acids (aa.), such as at least 20 aa., for example at least 25 aa., such as at least 30 aa., for example at least 35 aa., such as at least 40 aa., for example at least 45 amino acids.

In one embodiment, said a polypeptide or functionally equivalent subsequence of (a) is having a sequence identity of at least 85% to (a) or (b), such as at least 90% to (a) or (b), for example at least 95% to (a) or (b), such as at least 97% to (a) or (b), for example at least 98% to (a) or (b), such as at least 99% to (a) or (b).

The subsequence of the polypeptide encoded by SEQ ID NO. 1 has maintained the property of the parent polypeptide in terms of bactericidal and/or bacteriostatic properties (referred to as functionally equivalent). In one embodiment, the bactericidal and/or bacteriostatic activity of the subsequence is increased relative to the parent polypeptide. The bactericidal and/or bacteriostatic activity may be assessed using methods available in the art.

Other dinQ Peptide Variants.

Analysis of the DinQ amino acid sequence using the consensus secondary structure prediction tool Jpred3 revealed that DinQ has a high propensity to form a single alpha-helix. All residues except a few on each flanking terminal are predicted with high confidence to belong to the predicted alpha-helix. The structure may also be predicted using other prediction tools available to the skilled person.

The 3D structure of DinQ provided by the inventors may be used as a pharmacophore to design further DinQ variants such as a polypeptide or functionally equivalent subsequence of (a) is having a sequence identity of at least of 85% to (a) or (b), such as at least 90% to (a) or (b), for example at least 95% to (a) or (b), such as at least 97% to (a) or (b), for example at least 98% to (a) or (b), such as at least 99% to (a) or (b), where a polypeptide or functionally equivalent subsequence of (a)

Such functionally equivalent subsequences can include 5, such as 4, such as 3, such as 2, such as 1 modifications of the sequence. The modifications can be additions, substitutions or deletions.

The Polynucleotides of the Invention

The inventors provide polynucleotide (nucleic acid) sequences encoding the antibacterial DinQ polypeptides of the invention. The sequences may be used for a wide range of applications. Non-limiting examples are recombinant expression of the antibacterial polypeptides such as for further isolation of the recombinant antibacterial polypeptides, or for recombinant expression in the host bacteria in order to inhibit the growth or kill said bacteria.

The person skilled in the art would know when to employ the DNA sequences such as the cDNA sequence encoding the polypeptide and when to employ the corresponding RNA sequences.

Accordingly, one aspect of the present invention relates to an isolated polynucleotide comprising a nucleic acid sequence encoding an antibacterial polypeptide of the invention.

In one embodiment, the isolated polynucleotide encoding the DinQ polypeptide of the invention comprises a nucleic acid sequence selected from the group consisting of
   (a) SEQ ID NO. 2 (DinQ ORF-I CDS DNA sequence), SEQ ID NO. 4 (DinQ ORF-II CDS DNA sequence), SEQ ID NO. 6 (DinQ ORF-III CDS DNA sequence), SEQ ID NO. 8 (DinQ ORF-IV CDS DNA sequence), and SEQ ID NO. 10 (DinQ ORF-V CDS DNA sequence), (b) a nucleic acid sequence with a sequence identity of at least 85% to (a) and encoding a functionally equivalent polypeptide.

Examples of functionally equivalent polypeptides are provided with the peptide set forth in SEQ ID NO. 19 to 27. It follows that any polynucleotide comprising nucleic acid sequence encoding a peptide selected from the list consisting of SEQ ID NO. 19, SEQ ID NO. 20, SEQ ID NO. 21, SEQ ID NO. 22 SEQ ID NO. 23 SEQ ID NO. 24 SEQ ID NO. 25 SEQ ID NO. 26 and SEQ ID NO. 27 also an embodiment of the present invention.

In line with this, in one embodiment of the present invention the nucleic acid sequence is SEQ ID NO. 10 (DinQ ORF-V CDS DNA sequence), where the start codon (GTG) is substituted the with a ATG start codon.

In one embodiment, the isolated polynucleotide limited or essentially limited to the cited coding sequences (CDS).

In one embodiment, the polynucleotide comprises a nucleic acid sequence encoding an antibacterial polypeptide with the proviso that said polynucleotide does not encode SEQ ID NO. 3 (DinQ ORF-I peptide).

In another embodiment, said isolated polynucleotide is a molecule of RNA. It follows that the cited SEQ IDs are provided in the DNA format corresponding to the complementary DNA of said RNA. Accordingly, in one embodiment the SEQ IDs of the invention refers to the DNA sequences and in another embodiment the SEQ IDs are used to refer to the corresponding RNA sequences.

In another embodiment, the nucleic acid sequence of (b) is selected from the group consisting of a nucleic acid sequence having at least 90% sequence identity to (a) and encoding a functionally equivalent polypeptide, a nucleic acid sequence having at least 95% sequence identity to (a) and encoding a functionally equivalent polypeptide, a nucleic acid sequence having at least 97% sequence identity to (a) and encoding a functionally equivalent polypeptide, a nucleic acid sequence having at least 98% sequence identity to (a) and encoding a functionally equivalent polypeptide, a nucleic acid sequence having at least 99% sequence identity to (a) and encoding a functionally equivalent polypeptide.

The inventors disclose the presence of four native dinQ transcripts that encodes the antibacterial polypeptides of the invention. The transcript are referred to as dinQ-a (corresponding DNA sequence is SEQ ID NO. 14), dinQ-b (corresponding DNA sequence is SEQ ID NO. 15), dinQ-c, and dinQ-d (corresponding DNA sequence is SEQ ID NO. 16).

The dinQ-b (SEQ ID NO. 15) is the most abundant of the dinQ transcripts in the agrB mutant genetic background and produces a highly toxic peptide of 27 amino acids (SEQ ID NO. 13). Data from Northern blots, primer extension and in vitro transcription/translation analysis, performed by the inventors, demonstrate that translation is only detectable from the dinQ-b transcript. Further analysis of the primary sequence of dinQ-b (SEQ ID NO. 15) shows that a Shine-Delgarno sequence is present in the primary sequence around the alternative start codon GTG.

In another embodiment, the isolated polynucleotide is selected from the group consisting of SEQ ID NO. 14 (DinQ full length transcript, DinQ-a), SEQ ID NO. 15 (DinQ-b transcript), and SEQ ID NO. 16 (DinQ-d transcript).

In yet another embodiment, the isolated polynucleotide is selected from the group consisting of SEQ ID NO. 14 (DinQ full length transcript, DinQ-a), SEQ ID NO. 15 (DinQ-b transcript), SEQ ID NO. 16 (DinQ-d transcript), SEQ ID NO. 2 (DinQ ORF-I CDS DNA sequence) SEQ ID NO. 4 (DinQ ORF-II CDS DNA sequence), SEQ ID NO. 6 (DinQ ORF-III CDS DNA sequence), SEQ ID NO. 8 (DinQ ORF-IV CDS DNA sequence), and SEQ ID NO. 10 (DinQ ORF-V CDS DNA sequence). In a further embodiment, the isolated polynucleotides is essentially a polynucleotide selected from the group consisting of SEQ ID NO. 14 (DinQ full length transcript, DinQ-a), SEQ ID NO. 15 (DinQ-b transcript), SEQ ID NO. 16 (DinQ-d transcript), SEQ ID NO. 2 (DinQ ORF-I CDS DNA sequence) SEQ ID NO. 4 (DinQ ORF-II CDS DNA sequence), SEQ ID NO. 6 (DinQ ORF-III CDS DNA sequence), SEQ ID NO. 8 (DinQ ORF-IV CDS DNA sequence), and SEQ ID NO. 10 (DinQ ORF-V CDS DNA sequence).

agrA and agrB

The arsR-gor intergenic region contains two small RNAs, agrA and agrB, which are transcribed in the opposite direction to dinQ.

The inventors provide two small 85 nt RNAs, agrA and agrB with antisense homology to the dinQ gene. The agrB mutant is sensitive to UV irradiation, whereas the agrA and dinQ single mutants showed no sensitivity. The deletion of dinQ in the agrB background relieved the UV sensitivity of the agrB single mutant, suggesting that enhanced levels of the dinQ transcript due to deficient RNA interference increase UV sensitivity of the agrB single mutant. Moreover, overexpressing the dinQ gene in wild type cells increases UV-sensitivity, supporting that constitutive expression of dinQ modulates (antagonizes) the cellular protection to UV exposure.

The polynucleotide set forth by the SEQ ID NO. 12 (agrA encoding sequences) and SEQ ID NO. 13 (agrB encoding sequences) of the present invention encodes non-coding RNAs.

One embodiment of the present invention provides functionally equivalent subsequence of a polynucleotide according to SEQ ID NO. 12 or 13 (agrA and agrB gene sequence), said subsequence having at least the length of 15 nucleic acids, such as at least 20 nucleic acids, for example at least 25 nucleic acids, such as at least 30 nucleic acids, for example at least 35 nucleic acids, such as at least nucleic acids, such as at least 45 nucleic acids, such as at least 50 nucleic acids, such as at least 55 nucleic acids, such as at least 60 nucleic acids, such as at least 65 nucleic acids, such as at least 70 nucleic acids, such as at least 75 nucleic acids, such as at least 80 nucleic acids, for example at least 83 nucleic acids.

In one embodiment, said a polynucleotide or functionally equivalent subsequence of (a) is having a sequence identity of at least 85% to SEQ ID NO. 12 or 13, such as at least 90% to SEQ ID NO. 12 or 13, for example at least 95% to SEQ ID NO. 12 or 13, such as at least 97% to SEQ ID NO. 12 or 13, for example at least 98% to SEQ ID NO. 12 or 13, such as at least 99% to SEQ ID NO. 12 or 13.

One aspect of the invention relates to a method for reducing the load of or inhibition of propagation of a bacterium by increasing the activity (e.g. increasing the intracellular concentration) of an antibacterial peptide encoded by SEQ ID NO. 1 (dinQ gene sequence) in said bacterium.

Sequence Identity

In one embodiment the present invention relates to polypeptides having functionally equivalent sequence or subsequences of the sequences mentioned herein, such as but not limited to a functionally equivalent polypeptide with a sequence identity of at least 85%.

The term "sequence identity" indicates a quantitative measure of the degree of homology between two amino acid sequences or between two nucleic acid sequences of equal length. If the two sequences to be compared are not of equal length, they must be aligned to give the best possible fit, allowing the insertion of gaps or, alternatively, truncation at the ends of the polypeptide sequences or nucleotide sequences. The sequence identity can be calculated as $$\frac{(N_{ref} - N_{dif})100}{N_{ref}},$$

wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Ndif=2 and Nref=8). A gap is counted as non-identity of the specific residue(s), i.e. the DNA sequence AGTGTC will have a sequence identity of 75% with the DNA sequence AGTCAGTC (Ndif=2 and Nref=8).

With respect all embodiments of the invention relating to nucleotide sequences, the percentage of sequence identity between one or more sequences may also be based on alignments using any suitable software such as the clustalW software (http://www.ebi.ac.uk/clustalW/index.html) with default settings. For nucleotide sequence alignments these settings are: Alignment=3Dfull, Gap Open 10.00, Gap Ext. 0.20, Gap separation Dist. 4, DNA weight matrix: identity (IUB).

Alternatively, and as illustrated in the examples, nucleotide sequences may be analysed using any suitable software such as DNASIS Max and the comparison of the sequences may be done at http://www.paralign.org/. This service is based on the two comparison algorithms called Smith-Waterman (SW) and ParAlign. The first algorithm was published by Smith and Waterman (1981) and is a well established method that finds the optimal local alignment of two sequences. The other algorithm, ParAlign, is a heuristic method for sequence alignment; details on the method is published in Rognes (2001). Default settings for score matrix and Gap penalties as well as E-values were used.

When referring to complementary sequences, the following base pairing rules can be applied, G pairs to C and U, A pairs to T and U. "Nucleic acids sequence" and "polynucleotide sequence" are interchangeable terms in the context of the present invention.

The Application of the Polypeptides

DinQ polypeptides display toxic properties upon in vivo expression. agrB and agrA negatively regulates dinQ expression. Thus by decreasing the activity (e.g. concentration) of agrA or agrB in the bacteria, DinQ expression is subsequently up-regulated.

The inventors discovered that the DinQ polypeptides caused depolarization and ATP depletion of in the bacteria. The DinQ polypeptides of the invention may therefore be used in the following applications.

A primary usage is in maintaining plasmids in a large bacterial cell culture. Segregational stability may be increased compared to a control culture lacking a toxin-antitoxin system.

In large scale microorganism processes such as fermentation, progeny cells lacking the plasmid insert often have a higher fitness than those who inherit the plasmid and can outcompete the desirable microorganisms. A toxin-antitoxin system maintains the plasmid thereby maintaining the efficiency of the industrial process.

Additionally, toxin-antitoxin systems may be a future replacement for antibiotic selection.

Inducing suicide modules against pathogens could help combat the growing problem of multi-drug resistance.

Toxin-antitoxin assays may be developed to characterise toxin potency. Antitoxin is used in conjunction with a toxin to find the amount needed to neutralise a set amount of toxin. This technique was applied to the paralysis toxin of the paralysis tick of Australia, *Ixodes holocyclus*.

Ensuring a plasmid accepts an insert is a common problem of DNA cloning. Toxin-antitoxin systems can be used to positively select for only those cells which have taken up a plasmid containing the inserted gene of interest, screening out those which lack the inserted gene. Thus, cells containing the plasmid but not the insert will perish due to the toxic effects, and only those which have incorporated the insert will survive.

Genetically modified organisms must be contained in a pre-defined area during research. Toxin-antitoxin systems can be used to cause cell suicide upon certain conditions, such as a lack of a lab-specific growth medium which they would not encounter outside of the controlled laboratory set-up.

In one embodiment, the polypeptide, polynucleotide or the phagemid or bacteriophage of the present invention is for in vivo, ex vivo, in vitro or topical use.

A topical application is application to body surfaces such as the skin or mucous membranes such as the vagina, anus, throat, eyes and ears.

In vitro refers to studies in experimental biology that are conducted using components of an organism that have been isolated from their usual biological context in order to permit a more detailed or more convenient analysis than can be done with whole organisms. Colloquially, these experiments are commonly referred to as "test tube experiments".

In contrast, the term in vivo refers to work that is conducted with living organisms in their normal, intact state, while ex vivo refers to studies on functional organs that have been removed from the intact organism.

In a particular embodiment, the DinQ polypeptide of the invention or polynucleotide encoding an DinQ polypeptide of the invention, polynucleotide or vector encoding the same are used in combination with a least one antibiotic.

In an embodiment of the present invention is the antibiotic selected from the group consisting of: rifamycine, aminoglycosides, carbapenems, cephalosporins, cephems, glycopeptides, fluoroquinolones/quinolones, macrolides, oxazolidinones, penicillins, streptogramins, sulfonamides, tetracyclines, nalidixic acid, mitomycin C, ampicillin, and metabolic inhibitors such as erythromycin.

An aspect of the present invention relates to a method of treating a bacterial infection in a subject, said method comprising the step of administering to said subject the pharmaceutical composition of the present invention or the bacteriophage of the present invention.

An embodiment of the present invention comprises a further step of administering to said subject an effective amount of at least one other antibiotic.

Another aspect of the present invention relates to an in vitro method for reducing the load of or inhibition of propagation of a bacterium, comprising introducing the bacteriophage of the present invention in said bacterium.

Another aspect of the present invention relates to the use of a phagemid or bacteriophage of the present invention for reducing the load of or inhibiting the propagation of a bacterium in vitro.

It should be understood that any feature and/or aspect discussed in connection with the implementation of antisense molecules apply by analogy to heterologous expression using a vector or a phage expressing these antisense molecules for applications of the invention.

EXAMPLES

Figure 3:
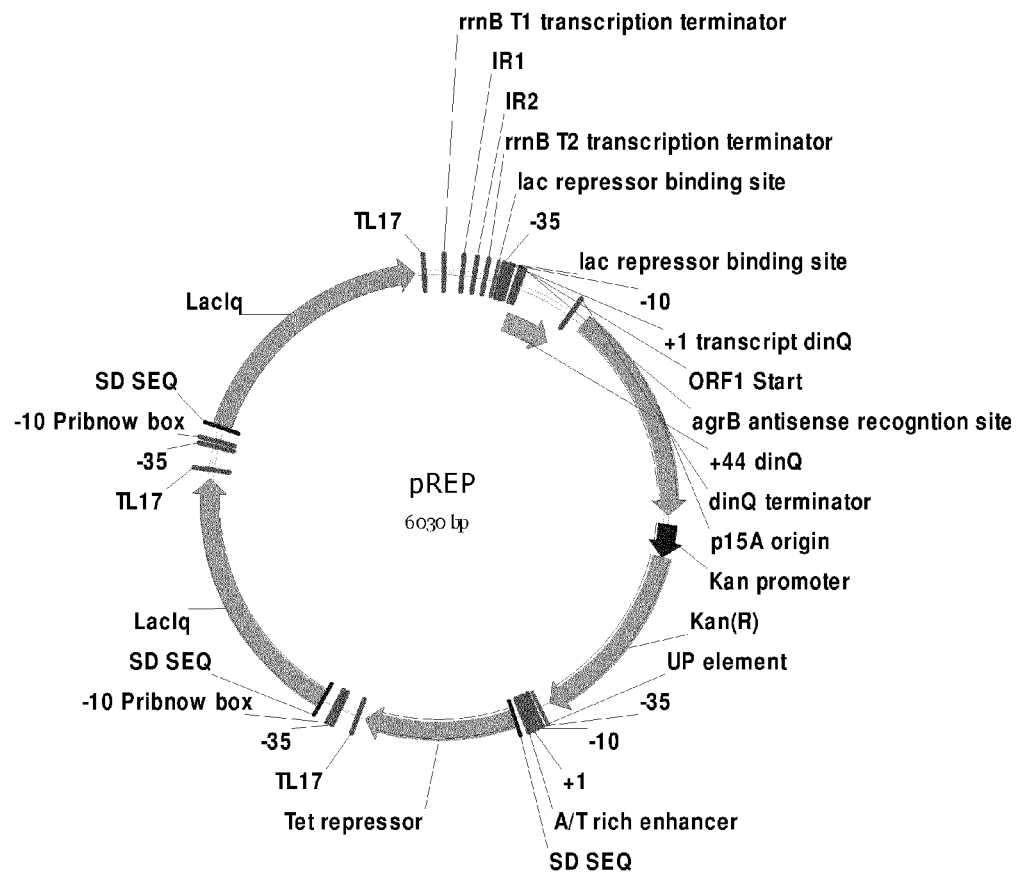

Example 1 pREP, FIG. 3, is transformed into ER2738 cells. Following production of electrocompetent cells, ER2738 pREP, these are transformed with pO5uniqREagrB, FIG. 4.

The antibiotic selection is tetracycline in ER2738 for the maintenance of the f-plius, kanamycin for pREP and pREP should therefore select for pO5uniqREagrB.

The production of the dinQ in pREP is suppressed until the introduction of IPTG.

The use of a tetracycline repressor sensitive operator for the antimicrobial peptide variant of dinQ means that its transcription remains repressed.

The newly generated strains are then followed over time to check for the maintenance of the plasmid.

This is done by extracting the plasmids from the cells, cutting with restriction endonucleases to check the identity of the plasmids present.

Example 2

The two panels of FIG. 5 use the same data, the difference being the notation which is explained below.

The rows of bacterial spots represent a 10-fold dilution series where the spots from left to right in each row in each grey box represent a 10-fold dilution of the previous spot to the left.

The spots with the highest bacterial concentrations, therefore, are the ones on the left of each row in each grey square.

This also means that the spots furthest to the right represent a 1/100 000 dilution of the original spot. From top to bottom of each square are six strains.

The top three are based on the AB1157 (denoted as wt above, lower panel) genetic background and the bottom three on the AB1157 background where the sRNA (small RNA) agrB (SEQ ID NO. 13) controlling the expression of dinQ has been removed, this is referred to as BK4043 (also denoted as agrB in the lower panel).

The effect of removing the agrB sRNA is that it causes a non-lethal overexpression of dinQ in the non-induced state, so in our case a genome based expression of the toxin dinQ.

Each of these strains has been complemented with one of the following three plasmids: pKK232-8, a commercially available expression system, the background for this experiment, pBK445 & pBK446 that are the same apart from that they contain the genetic sequence for agrA (SEQ ID NO. 12) and agrB (SEQ ID NO. 13) respectively.

These are the antitoxin sRNA elements.

The squares from left to right then show replicates of the same bacteria as seen in the boxes to the left exposed to different quantities (J/m2) of UV (ultraviolet) radiation.

Exposure to UV increases the expression of dinQ, the toxin, to lethal levels, this is easily seen above in the disappearance of the spots from the BK4043/pKK232-8 strain, i.e. where only the toxin is present.

Where the toxin is complemented with either the antitoxin agrA (SEQ ID NO. 12) or agrB (SEQ ID NO. 13), i.e. pBK445 or pBK446 the level of toxicity is similar to the wild type (AB1157/pKK232-8), showing that the antitoxin is ablating the toxic effects of dinQ.

Example 3

Introduction of a plasmid based source of dinQ is not possible in a strain where the antitoxin agrB has been removed.

The strain BK4043, AB1157 agrB::kan, lacks the antitoxin sRNA agrB.

This in itself gives a non-lethal overexpression of dinQ.

The plasmid pBK444, pKK232-8 containing all dinQ ORFs and regulatory region but neither agrA or agrB sRNAs, once transformed into the bacteria results in a non-lethal overexpression of dinQ.

Figure 6:
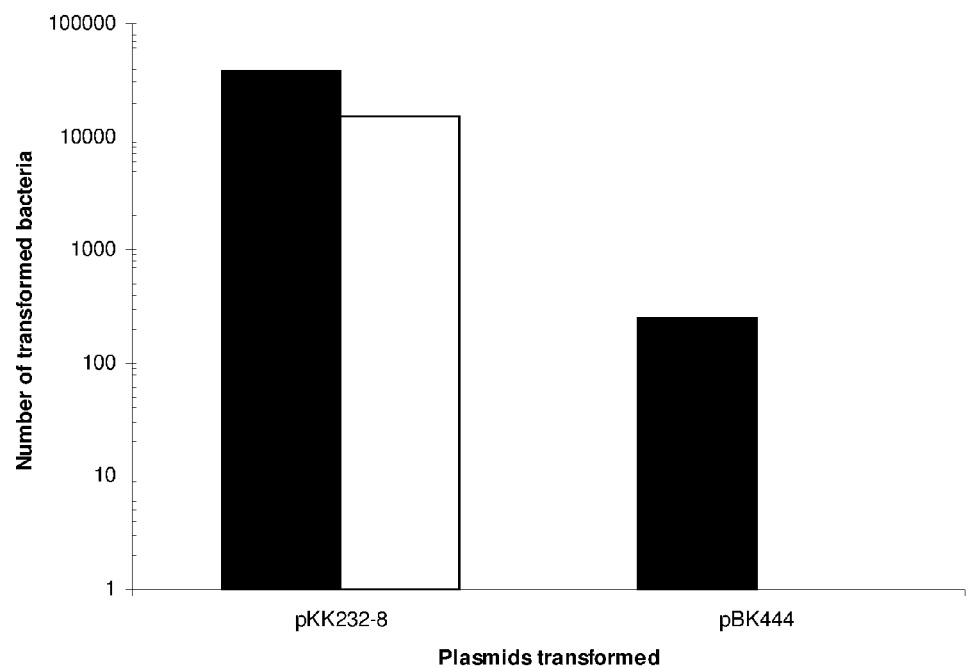

FIG. 6 demonstrates that the electroporation of pBK444 is possible in the original AB1157 strain, which can produce the sRNA agrB but not into BK4043 which lacks argB. This demonstrates that the sRNA agrB is required as an antitoxin to prevent the translation of the toxin.

Example 4

The removal of the antitoxin agrB following recombination results in fewer transformants due to the induction in translation of dinQ.

In order to create new strains an alternative gene is transformed into the bacteria containing homologous regions at the ends of the alternative gene.

Once recombined into the correct genetic locus the gene or sRNA will no longer be produced.

In the case of the removal of an antitoxin, in this case agrB, the concentration of the antitoxin will be rapidly reduced and eliminated.

This will therefore produce an overexpression of the toxin, dinQ.

The resultant toxicity will in many cases result in the elimination of the recombinants.

This is demonstrated here where in all instances agrB (agrB and, agrAB) is removed many fewer recombinants are detected due to the buildup of toxicity of DinQ.

The results can be seen in FIG. 6.

Example 5

The expression of a agrB expressing plasmid stabilises the strain BK4043 in both rich media (LB) and minimal media (M9 glucose).

The loss of the agrB expressing plasmid results in a significant growth disadvantage of these cells so resulting in their rapid elimination from culture.

Figure 7:
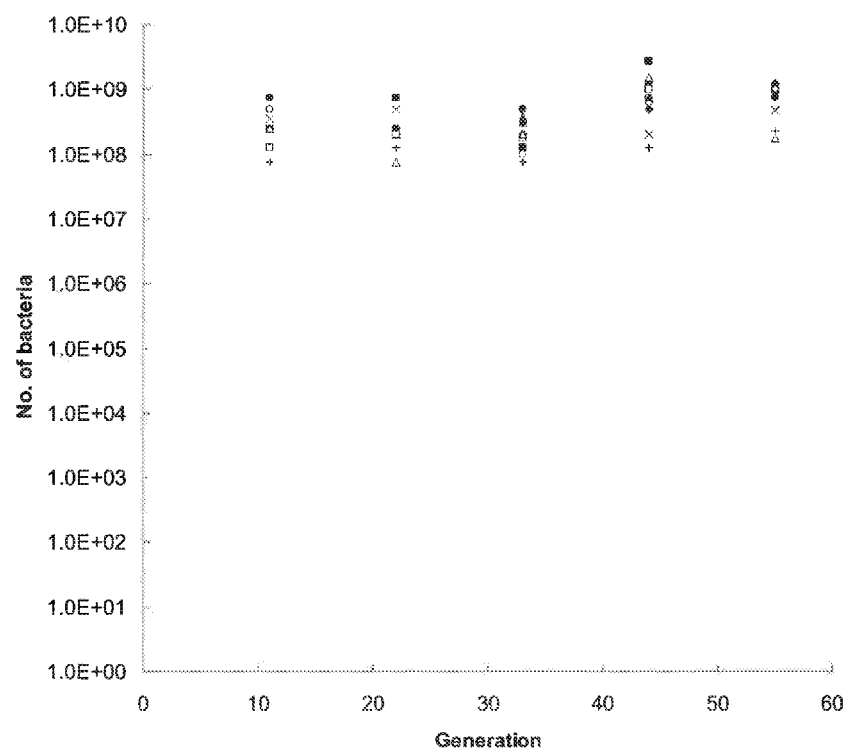

Stability of pBK446 (expresses agrB from its natural promoter) in BK4043 (a knockout of agrB that results in an over expression of dinQ) in both rich media (LB) and minimal media (M9, glucose) with either no selection (number of colonies ■, number of amp$^R$ colonies □) or 0.5 (▲, △), 1 (●, ○) & 2 (×,+) µg/ml Nalidixic acid. The results can be seen in FIG. 7.

A positive control using ampicillin selection was also included (◆, ◇).

Nalidixic acid, a synthetic quinolone antibiotics, inhibits a unit of DNA gyrase which results in double strand DNA breaks which in turn can induce the SOS response after end processing by recBCD.

Example 6

The plasmid expression of the entire dinQ locus including regulatory sRNAs agrA & agrB results in the stable maintenance of the plasmid.

These growth defects then result in the elimination of the plasmid free bacteria from solution. Stability of pBK440 (expresses the entire dinQ region including agrAB) in AB1157 in both rich media (LB) and minimal media (M9, glucose) with either no selection (number of colonies ■, number of amp$^R$ colonies □) or 0.5 (▲,△), 1 (●, ○) & 2 (×,+) μg/ml Nalidixic acid. A positive control using ampicillin selection was also included (♦, ◇).

Figure 8:
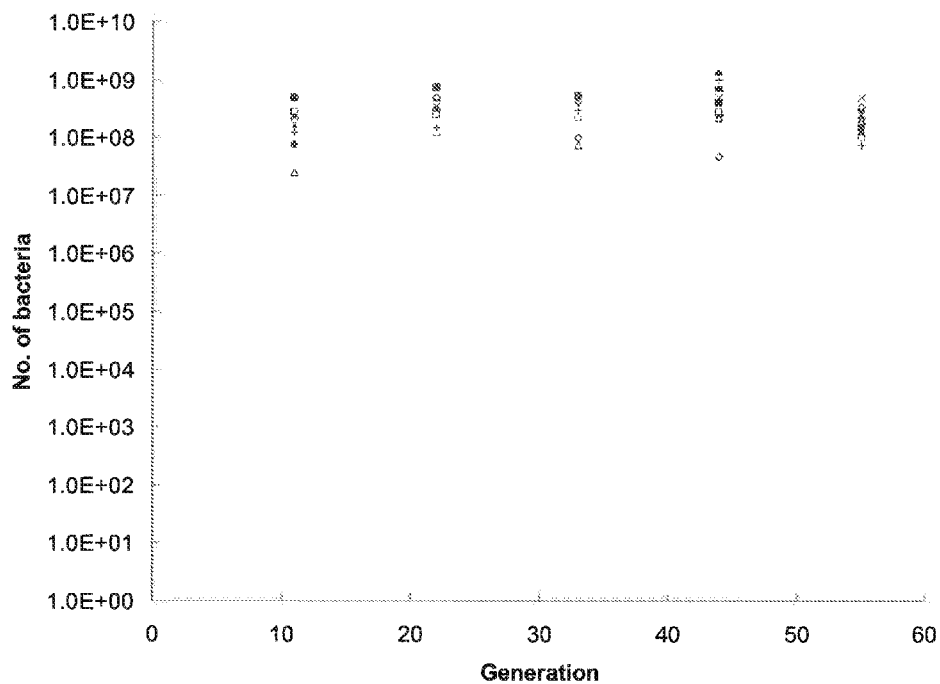

The results can be seen in FIG. 8.

Example 7

The plasmid expression of the entire dinQ locus including regulatory sRNAs agrA & agrB results in the stable maintenance of the plasmid.

These growth defects then result in the elimination of the plasmid free bacteria from solution. Stability of pBK440 (expresses the entire dinQ region including agrAB) in MG1655 in both rich media (LB) and minimal media (M9, glucose) with either no selection (number of colonies ■, number of amp$^R$ colonies □) or 0.5 (▲,△), 1 (●, ○) & 2 (×,+) μg/ml Nalidixic acid. A positive control using ampicillin selection was also included (♦, ◇).

Figure 9:
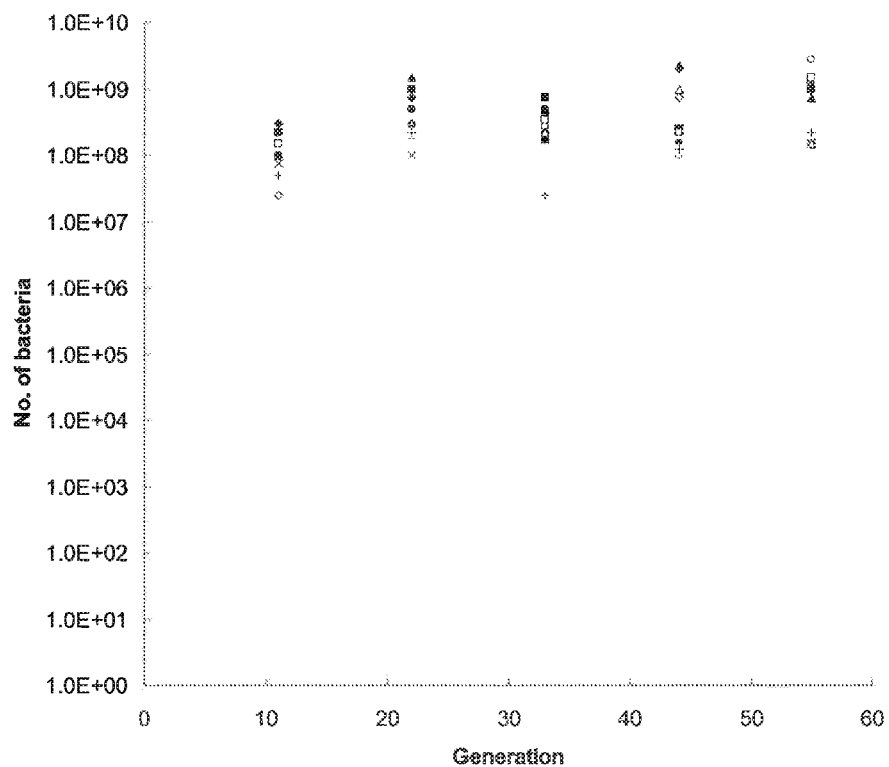

The results can be seen in FIG. 9.

Example 8

Instability of pBK444 in MG1655, example of a toxic construct in both LB and minimal media+glucose with either no selection, 1 or 2 μg/ml Nalidixic acid.

Figure 10:
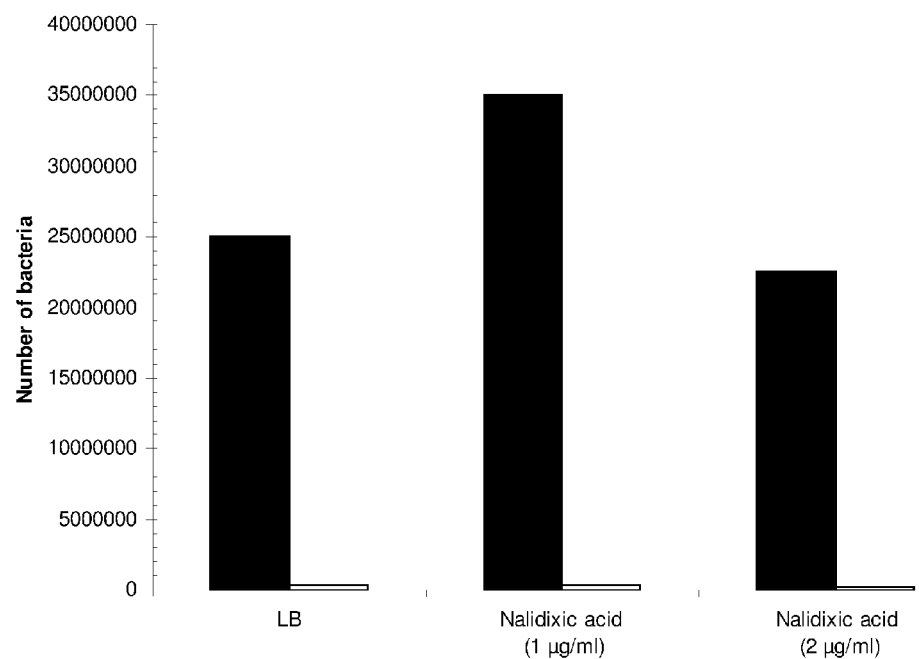

The results can be seen in FIG. 10.

Example 9

Synthetic TA System pO5uniqREagrB/pREP System.

System is lethal with pO5uniqREagrB or pREP alone due to the toxicity of +44 dinQ and due to the lack of repression of ORF5 dinQ. However, in the presence of each other they do not compromise the viability of the host bacteria.

Figure 4:
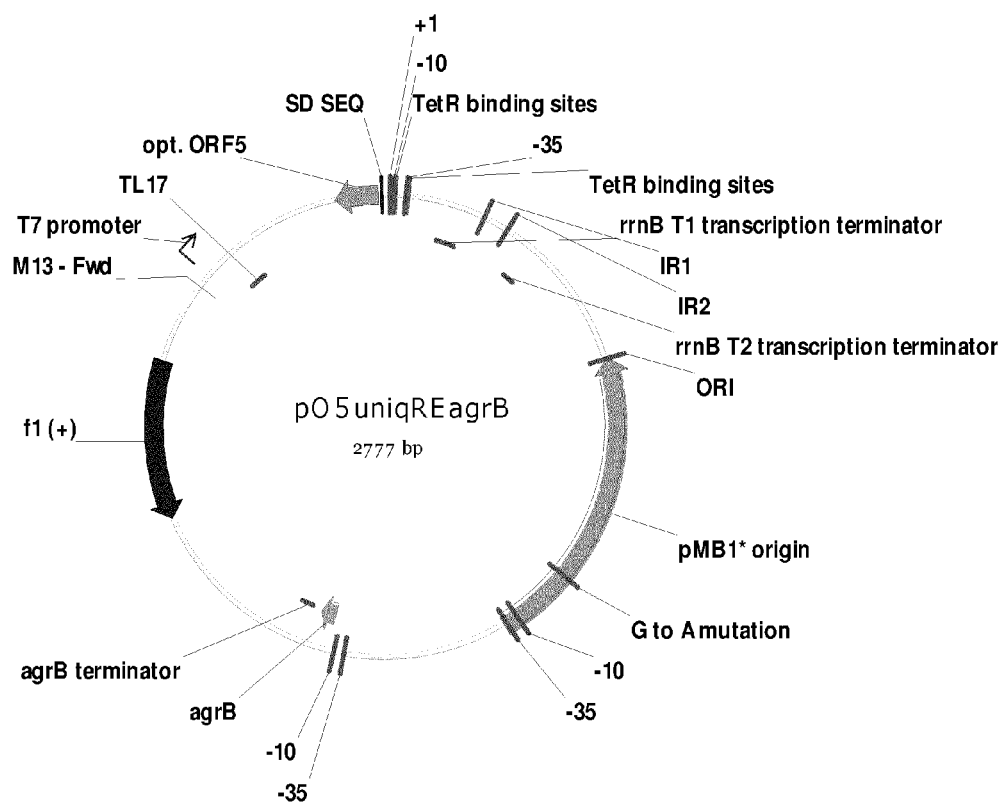

The basic idea of this system is described in FIGS. 3 and 4.

Example 10

Toxic, dinQ Related, Sequences

It has been observed that some sequence variation is tolerated when looking for similarly toxic peptides related to dinQ.

Those sequences that have been examined are listed below, the amino acid changes with regards to the reference are underlined.

Amino Acid Sequences

Original

```
                                              (SEQ ID NO. 13)
        MIDKAIIVLGALIALLELIRFLLQLLN
```

Similarly Toxic

```
                                              (SEQ ID NO. 21)
        MIDKAIVVLGALIALLELIRFLLQLLN (SEQ ID NO. 19)
        MIDKAIIVLKALIALLELIRFLLQLLN (SEQ ID NO. 23)
        MIDKAIIVLNALIALLELIRFLLQLLN (SEQ ID NO. 22)
        MIDKAIIVLGAIVALLELIRFLLQLLN (SEQ ID NO. 20)
        MIDKAIIVLGALIALLELIRFLIQLLN
```

Partially Toxic

```
                                              (SEQ ID NO. 24)
        MIRKAIIVLGALIALLELIRFLLQLLN (SEQ ID NO. 25)
        MIDKAIIVLGALIAVLELIRFLLQLLN (SEQ ID NO. 26)
        MIDKAIIVLGALIALLELVRFLLQLLN (SEQ ID NO. 27)
        MIDKAIIVLGALIALLELIRFILQLLN
```

The invention claimed is:

1. One or more plasmids comprising a dinQ-sRNA type I toxin-antitoxin system, wherein the one or more plasmids comprise polynucleotide sequences encoding for dinQ and an sRNA selected from agrA or agrB.

2. The one or more plasmids according to claim 1, wherein the toxin and the antitoxin polynucleotide sequences are comprised in different plasmids.

3. The one or more plasmids according to claim 1, wherein the toxin and the antitoxin polynucleotide sequences are comprised in the same plasmid.

4. A dinQ-sRNA type I toxin-antitoxin system comprising chromosomally expressed sRNA selected from agrA or agrB and one or more plasmids comprising polynucleotide sequences encoding dinQ.

5. The plasmid selection system according to claim 1, wherein the dinQ nucleic acid sequence is selected from the group consisting of SEQ ID NO. 3, SEQ ID NO. 5, SEQ ID NO. 7, SEQ ID NO. 9, SEQ ID NO. 11, SEQ ID NO. 12, SEQ ID NO. 13, SEQ ID NO. 14, SEQ ID NO. 15, SEQ ID NO. 17, SEQ ID NO. 18, SEQ ID NO. 19, SEQ ID NO. 20, SEQ II) NO. 21, SEQ ID NO, 22, SEQ ID NO. 23, SEQ ID NO. 24, SEQ ID NO. 25, SEQ ID NO. 26 and SEQ ID NO. 27.

* * * * *